United States Patent [19]

Takamura et al.

[11] Patent Number: 4,993,405
[45] Date of Patent: Feb. 19, 1991

[54] IMAGING APPARATUS

[75] Inventors: Kohji Takamura, Hachioji; Kiyoshi Tsuji, Musashino, both of Japan

[73] Assignee: Olympus Optical Co., Ltd., Tokyo, Japan

[21] Appl. No.: 514,642

[22] Filed: Apr. 25, 1990

[30] Foreign Application Priority Data

May 15, 1989 [JP] Japan .................................. 1-120870

[51] Int. Cl.⁵ .............................................. A61B 1/04
[52] U.S. Cl. .......................................... 128/6; 358/98
[58] Field of Search ........................... 128/4, 6; 358/98

[56] References Cited

U.S. PATENT DOCUMENTS 4,646,723  3/1987  Arakawa ................................. 128/6

FOREIGN PATENT DOCUMENTS 63-272180 11/1988 Japan .
1-222579   9/1989 Japan .

Primary Examiner—William H. Grieb
Attorney, Agent, or Firm—Armstrong, Nikaido, Marmelstein, Kubovcik & Murray

[57] ABSTRACT

An imaging apparatus comprising a solid state imaging device for imaging an object image, an electronic circuit connected operatively to the solid state imaging device and generating heat and a heat conducting member leading the heat generated from the electronic circuit in a direction different from the solid state imaging device side at a thermal conductivity higher than the thermal conductivity of the heat generated from the electronic circuit to the solid state imaging device side.

17 Claims, 12 Drawing Sheets

IMAGING APPARATUS

BACKGROUND OF THE INVENTION

1. Field of the Invention:

This invention relates to an imaging apparatus having a solid state imaging device.

2. Related Art Statement:

Recently there is extensively used an endoscope apparatus whereby, by inserting an elongate insertable part into a body cavity, the body cavity interior can be observed or, as required, by using a treating instrument, a therapeutic treatment can be made or, by inserting the above mentioned insertable part into a pipe hole, the interior of the pipe hole can be observed.

Among such endoscope apparatus, there are an optical endoscope in which, for example, a fiber bundle is used as a transmitting optical system and an electronic endoscope in which such solid state imaging device as a charge coupled device (CCD) is used as an imaging apparatus.

This electronic endoscope has advantages that it is higher in the resolution and is easier to record, reproduce, magnify and compare images than the optical endoscope.

As disclosed in the publication for example, of Japanese Patent Application Laid Open No. 2721807/1988, the above mentioned solid state imaging device is fixed in an image forming position by an objective lens so that an optical image of an observed part formed by this objective lens may be photoelectrically converted by the above mentioned solid state imaging device and may be amplified by an amplifying circuit provided on a circuit substrate. This amplified signal is input into an image signal processing circuit within a video processor through a signal cable connected to the circuit substrate and is then output in a television monitor so that the image of the observed part may be observed through this television monitor.

However, the above mentioned amplifying circuit will generate heat during the operation. A regulator is arranged generally on the above mentioned circuit substrate and will also generate heat during the operation. When the heat of such heat generating parts as these amplifying circuit and regulator is transmitted to the solid state imaging device, the temperature of the solid state imaging device will rise to be above the standard operating temperature, heat noises will be generated, the image displayed in the television monitor will deteriorate and the durability of the solid state imaging device will also reduce.

For example, whereas the standard operating temperature of the above mentioned solid state imaging device is about 55° C., the using limit operating temperature of an amplifying IC which is an example of an amplifying circuit is above 70° C. and thus the solid state imaging device is lower in the heat capacity. In an experiment in case the amplifying circuit was supposed to be arranged adjacently to the solid state imaging device, the temperature of the solid state imaging device rose to about 58° C.

In order to cope with this, it may be considered to arrange the heat generating part in such part separated sufficiently from the solid state imaging device as on the hand base side or in the course of the above mentioned insertable part so that it may be difficult for the heat of the heat generating part to be transmitted to the solid state imaging device. However, when such heat generating part as the amplifying circuit and the solid state imaging device are separated from each other, the distance for transmitting signals will become longer, the outside turbulent noises will be more likely to come in and the apparatus will be likely to become larger.

As disclosed, for example, in U.S. Pat. No. 4,491,865, in the above mentioned electronic endoscope, a solid state imaging device is provided on a substrate, a signal line to be connected is fixed with a resin or the like on the back side of this substrate and the whole is sealed within a housing to mostly prevent fogging from being caused by a moisture mixed in and reinforce the strength of the housing.

Besides the above mentioned formation example, the housing is provided within it with a solid state imaging device, a driving circuit driving this solid state imaging device and an output buffer outputting a video signal converted by the solid state imaging device.

In such case, the frequency handled by the above mentioned driving circuit is so high that, in case such high capacity device as such solid state imaging device as a CCD is to be driven, it will be required to be driven at a particularly low impedance and therefore the generated heat amount will be large. Particularly, in an imaging apparatus in which the head part and the processing part processing a video signal are remotely connected with each other, the output buffer for transmitting the cable makes a low impedance conversion, that is, current amplification and therefore the generated heat amount is large. In most cases, this generated heat amount is larger than the generated heat amount by the solid imaging device. In such case, if the solid state imaging device and the substrate are filled with a resin or the like, the heat generated in the substrate will stay within the housing and will heat the solid state imaging device and, as a result, the S/N ratio will be reduced by the increase of a dark current and the heat generated noises will increase to be likely to deteriorate the picture quality.

OBJECT AND SUMMARY OF THE INVENTION

An object of the present invention is to provide an imaging apparatus wherein the temperature of the solid state imaging device is prevented from being elevated by the heat of the heat generating part so as to prevent the image from being deteriorated, the durability of the solid state imaging device from being reduced and the apparatus from being made large.

The imaging apparatus of the present invention comprises a solid state imaging device for imaging an object image, an electronic circuit operatively connected to the above mentioned solid state imaging device and generating heat and a heat conducting means for leading the above mentioned heat in a direction different from the above mentioned solid state imaging device, side at a thermal conductivity higher than the thermal conductivity to the above mentioned solid state imaging device side of the above mentioned heat generated from the above mentioned electronic circuit.

The other features and advantages of the present invention will become apparent enough with the following explanation.

BRIEF DESCRIPTION OF THE DRAWINGS

FIG. 1 is a sectioned view of an imaging apparatus.

FIG. 2 is a sectioned view of a tip part of an endoscope.

FIG. 3 is an elevation of the tip part of the endoscope.

FIG. 4 is an explanatory view showing the formation of an endoscope system.

FIG. 5 is an explanatory view showing an endoscope image when a forceps is used.

FIG. 6 is an explanatory view showing light distributing characteristics of an endoscope.

FIG. 7 is a circuit diagram showing an electronic circuit.

FIG. 12 is a sectioned view of an imaging apparatus.

FIG. 13 is a bottom view of FIG. 12.

FIG. 16 is a conceptional view showing a schematic formation of an imaging apparatus.

FIG. 17 is an explanatory view showing the formation of a camera head.

FIG. 18 is an explanatory view showing the formation of an endoscope system.

FIG. 22 is a side view showing the formation of an endoscope system.

FIG. 23 is a sectioned view of a tip part of an endoscope.

DETAILED DESCRIPTION OF THE PREFERRED EMBODIMENTS

In FIGS. 1 to 7 is shown the first embodiment of the present invention.

Figure 4:
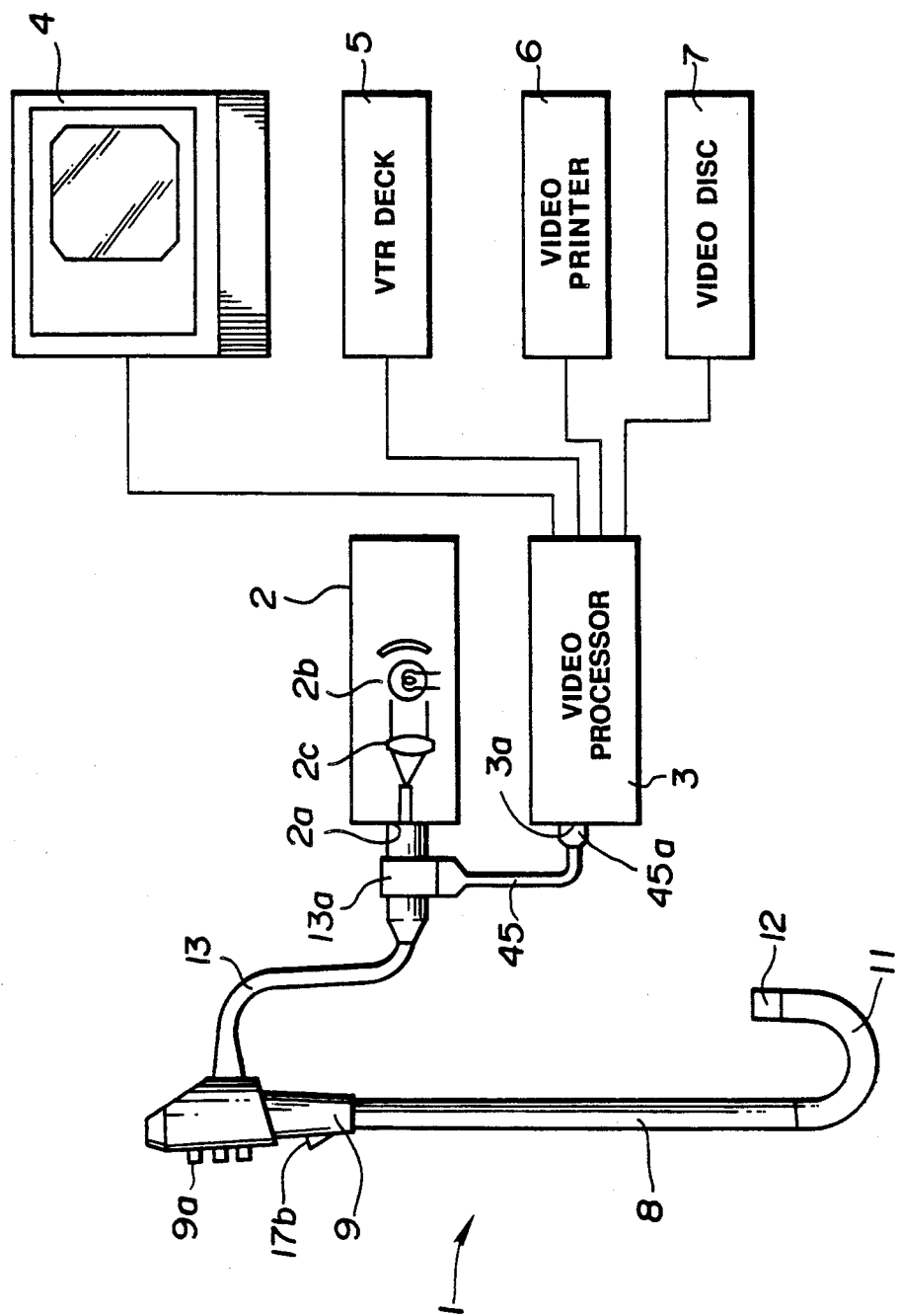

First of all, the summary of an endoscope system shall be explained with reference to FIG. 4. The endoscope system comprises an endoscope 1, a light source apparatus 2 to which this endoscope 1 is connected and a video processor 3 which has a video signal processing circuit and driving circuit built-in and to which are to be connected such peripheral devices as a monitor 4, VTR deck 5, video printer 6 and video disc 7.

Figure 2:
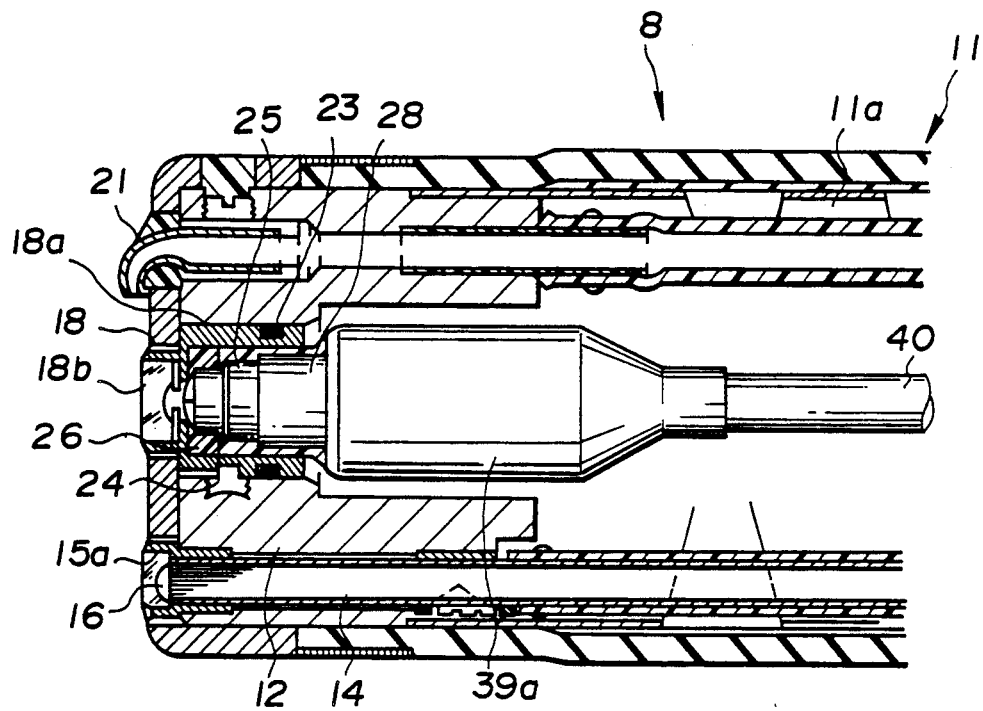

The above mentioned endoscope 1 has an elongate flexible insertable part 8 insertable into a body cavity and a thick operating part 9 connected to this insertable part 8 on the base end side. As shown in FIG. 2, the above mentioned insertable part 8 is provided on the tip side with a tip part 12 through a curvable part 11 formed of a plurality of joint rings 11a so that, by curving the curvable part with an angle lever not illustrated arranged on the above mentioned operating part 9, the above mentioned tip part 12 may directed to the part to be inspected.

A universal cord 13 having a connector device 13a at the tip is extended from one side of the above mentioned operating part 9. On the other hand, the above mentioned light source apparatus 2 is provided with a connector receptacle 2a to which this connector device 13a is connected. By connecting this connector device 13a and connector receptacle 2a with each other, the illuminating light generated by the light source lamp 2b of the light source apparatus 2 and condensed by the condenser lens 2c can be led toward the endoscope 1 through a light guide not illustrated arranged through the universal cord 13.

Figure 3:
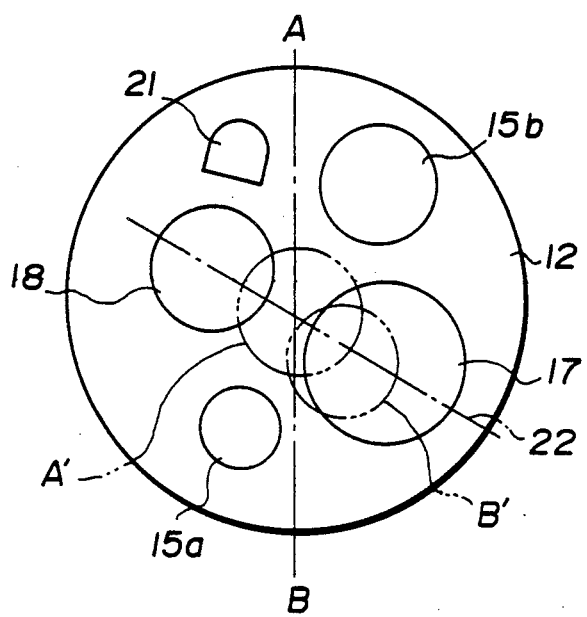

This light guide is branched into two light guides 14 arranged in a pair through the above mentioned insertable part 8 and extended to the above mentioned tip part 12. As shown in FIG. 3, a pair of illuminating through holes 15a and 15b are formed in positions deflected above and below in this tip part 12 so that the illuminating light by the above mentioned light source apparatus 2 may be radiated to the observed part through light distributing lenses 16 fixed in these illuminating through holes 15a and 15b.

A forceps through hole 17 is formed in a part held between the above mentioned pair of illuminating through holes 15a and 15b and deflected to the outer peripheral side of the tip part 12 and is made to communicate with a forceps inserting port 17b formed in the above mentioned operating part 9 through a forceps channel not illustrated arranged through the above mentioned insertable part so that the forceps inserted into this inserting port 17b may be projected out of the tip part 12 through the above mentioned forceps through hole 17.

Further, an observing through hole 18 fitted with a cover lens 18b through a first lens frame 18a is formed in this tip part 12 so that the observed part may be observed through this observing through hole 18. An air and water feeding nozzle 21 directed to the above mentioned cover lens 18b is provided in this tip part 12 so that, by operating switches 9a arranged on this operating part 9, air and water may be fed to the cover lens 18b through the above mentioned nozzle 21 to remove fogging or the like on this cover lens 18b surface.

Figure 5:
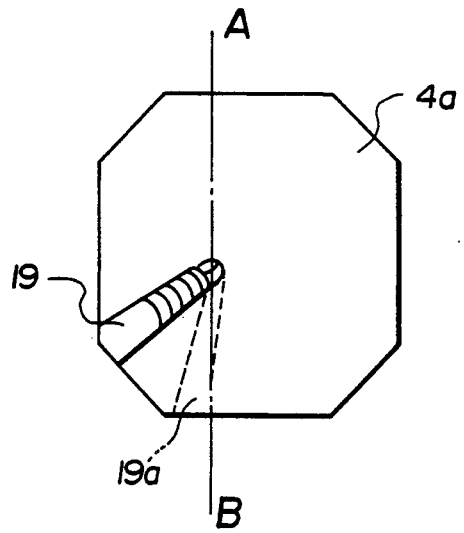
Figure 6:
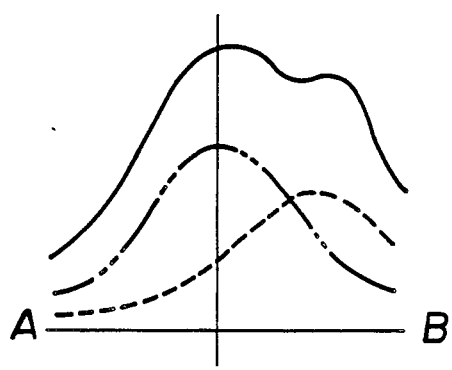

The above mentioned observing through hole 18 is formed in a position opposed to the above mentioned forceps through hole 17 with the center axis of the tip part 12 between. The above mentioned illuminating through hole 15a formed in the lower part of the tip part 12 to make the tip part 12 small in the diameter is made smaller in the diameter than the other illuminating through hole 15b formed on the upper side of the tip part 12 so that, when the illuminating light is uniformly radiated from these illuminating through holes 15a and 15b, the light amount radiated through the observing through hole 15b of the larger diameter will be larger than the light amount radiated through the illuminating through hole 15a of the smaller diameter and, as shown in FIG. 5, in the case of a therapeutic treatment with the forceps 19, a shadow 19a of the forceps 19 will be produced in the image observed through the above mentioned observing through hole 18 and will be likely to obstruct the observation and therapy.

In this embodiment, the above mentioned problem is coped with by making illuminating lights radiated through the above mentioned illuminating through holes 15a and 15b have respective peaks. That is to say, as shown by the two-point chain line in FIG. 6, the illuminating light radiated from the illuminating through hole 15b provided in the upper part of the tip part 12 is so set that the peak of the light distribution may come to the position in which the center line A-B in the perpendicular direction of the tip part 12 and the line 22 connecting the center lines of the above mentioned objective lens 18 and forceps through hole 17 intersect with each other, that is, to the position A' in FIG. 3. On the other hand, as shown by the broken line in FIG. 6, the light distribution peak of the illuminating light radiated from the illuminating through hole 15a of a comparatively smaller diameter provided in the lower part of the tip part 12 is so set as to come to the position deflected to the forceps through hole 17 side on the above mentioned line 22, that is, to the position shown by B' in FIG. 3. As a result, the illuminating light from the above mentioned illuminating through hole 15a will be radiated below the forceps 19 shown in FIG. 5 and the shadow 19a will be prevented from being produced in this position.

Figure 1:
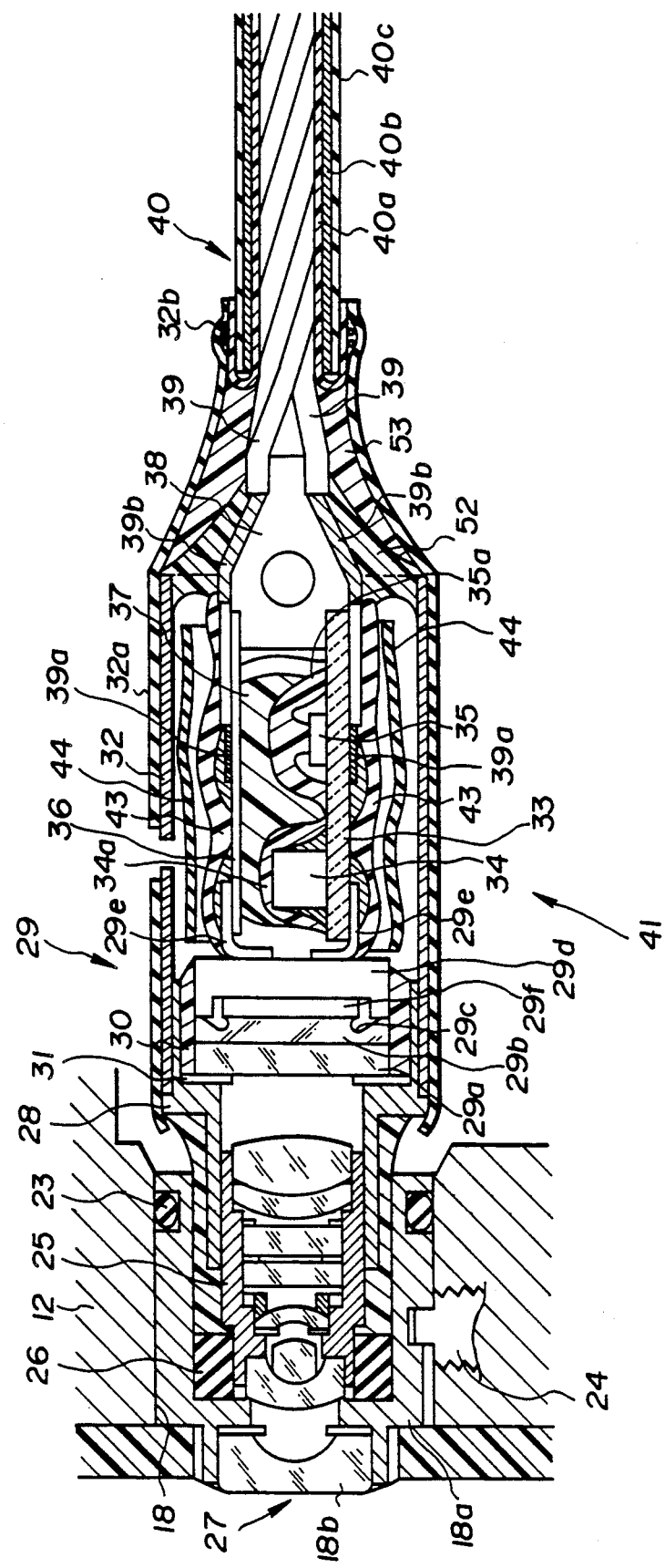
FIGS. 1 to 7 relate to the first embodiment of the present invention.

On the other hand, as shown in FIGS. 1 and 2, the above mentioned first lens frame 18a is fixed to the observing through hole 18 with a fixing screw 24 and an O-ring 23 is interposed between the observing through hole 18 and the first lens frame 18a so that a liquid-tight state may be held by this ring 23 within the observing through hole 18.

Also, a second lens frame 25 is fixed through an insulating member 26 on the side opposite the cover lens 18b of the above mentioned first lens frame 18a. An objective lens system 27 formed of a plurality of lens groups having an optical axis coinciding with the axis of the observing through hole 18 and the optical axis of the cover lens 18 is arranged within this second lens frame 25. A device frame 28 is fixed as crowned on the outer periphery on the side opposite the lens frame 18a of this second lens frame 25 and is extended out in the rear of this second lens frame 25. In this extended part, a solid state imaging device 29 intersects at right angles with the optical axis of the above mentioned objective lens system 26 and is fixed with a bonding agent 30.

This solid state imaging device 29 comprises a cover glass 29a arranged on the above mentioned objective lens system 26 side, a transparent sealing resin 29b provided on the side opposite the objective lens system 26 of this cover glass 29a and a device chip 29f fixed to the sealing resin 29b through bonding wires 29c and led to a plurality of external leads 29e through an internal wiring of a device substrate 29d. On the objective lens system 27 side of the above mentioned cover glass 29a is provided a flare iris 31 by which the lightness of the image incident through the above mentioned objective lens system 27 is regulated.

A shield frame 32 formed to be cylindrical and covered on the outer periphery with an insulating cover 32a is fixed at the tip to the above mentioned device frame 28 on the base end side outer periphery and is extended out rearward on the base end side. Within this extended part, a circuit substrate 33 made of ceramics is held substantially parallelly with the above mentioned optical axis and is connected with the above mentioned external leads 29e.

A condenser 34 is arranged on the above mentioned solid state imaging device 29 side on this circuit substrate 33, is fixed to the circuit substrate 33 as connected by soldering to a circuit pattern within the circuit substrate 33 and is enclosed with an insulator 34a.

A signal amplifying IC 35 forming an amplifying circuit which is an example of a heat generating part is die-bonded to the part on the side opposite the above mentioned solid state imaging device 29 of the condenser 34, is then wire-bonded to the circuit pattern of the above mentioned circuit substrate 33 and is further covered with a sealing resin 35a. An electronic circuit 41 is formed of these condenser 34 and signal amplifying IC 35.

Within the above mentioned shield frame 32, a through substrate 36 is fixed substantially parallelly with the circuit substrate 33 and is led to the internal wiring of the device substrate 29d through the above mentioned external lead 29e. The space between this through substrate 36 and the above mentioned circuit substrate 33 is filled with a potting agent 37 for radiating heat. A cable fixing member 38 made of a metal is fixed by soldering to the through substrate 36 and circuit substrate 33 on the base end sides.

A signal transmitting cable 40 consisting of a plurality of cables 39 is extended from the base end side of the above mentioned shield frame 32. Outside conductors 39b of these cables 39 are in contact with the above mentioned cable fixing member 38. A plurality of inside conductors 39a of the above mentioned cables 39 are fixed by soldering respectively to the surface on the side opposite the circuit substrate 33 of the above mentioned through substrate 36, that is, to the upper surface of the through substrate 36 and to the surface on the side opposite the through substrate 36 of the circuit substrate 33, that is, to the lower surface of the circuit substrate 33.

Among the above mentioned plurality of inside conductors 39a the inside conductors 39a fixed to the circuit substrate 33 are fixed by soldering to the side opposite the above mentioned signal amplifying IC 35 of this circuit substrate 33 so that the heat generated by this signal amplifying IC 35 may be transmitted to the inside conductors 39a through the circuit substrate 33 and to the base end side of the insertable part 8 through the inside conductors 39a and the heat transmitted to the circuit substrate 33 may be transmitted to the above mentioned signal transmitting cable 40 and to the base end side of the insertable part 8 and may be thereby prevented from being transmitted to the above mentioned solid state imaging device 29 side and the temperature rise of this solid state imaging device 29 may be avoided.

Insulating members 43 are in close contact respectively with the upper surface of the above mentioned through substrate 36 and the lower surface of the circuit substrate 33 and are further enclosed on the outer periphery with an insulating tube 44.

On the other hand, the insulating cover 32a covering the above mentioned shield frame 32 is extended toward the base end beyond the shield frame 32, is reduced in the diameter and is fixed at the tip to the above mentioned signal transmitting cable 40 by a thread winding bonding part 32b. An electroconductive bonding agent 52 is set between the above mentioned shield frame 32 and the outside conductor 39b of the cable 39 and a reinforcing bonding agent 53 is set between the part extended to the base end side from the shield frame 32 and the above mentioned cable 39 so that the above mentioned cable 39 may be fixed.

In the above mentioned signal transmitting cable 40, a plurality of cables 39 are coated with an integral shielding member 40a, are fixed with a pressing winding member 40b and are coated on the outer periphery of the pressing winding member 40a with a cable sheath 40c.

This signal transmitting cable 40 is extended on the base end side to the connector device 13a of the universal cord 13 through the insertable part 8. As shown in FIG. 4, another universal cord 45 internally fitted with the extended part of the above mentioned signal transmitting cable 40 is extended out of this connector device 13a on one side and is provided at the tip with another connector device 45a. The above mentioned video processor 3 is provided with a connector receptacle 3a to which this connector device 45a is to be connected. The universal cord 45 internally fitted with the above mentioned signal transmitting cable 40 is to be connected to the above mentioned video processor 3 through this connector device 45a. When the image signal of the observed part photoelectrically converted by the above mentioned solid state imaging device 29 is processed in the signal processing circuit within the video processor 3 and is output to the monitor 4, the video image of the observed part will be able to be observed in the picture 4a of this monitor 4.

Figure 7:
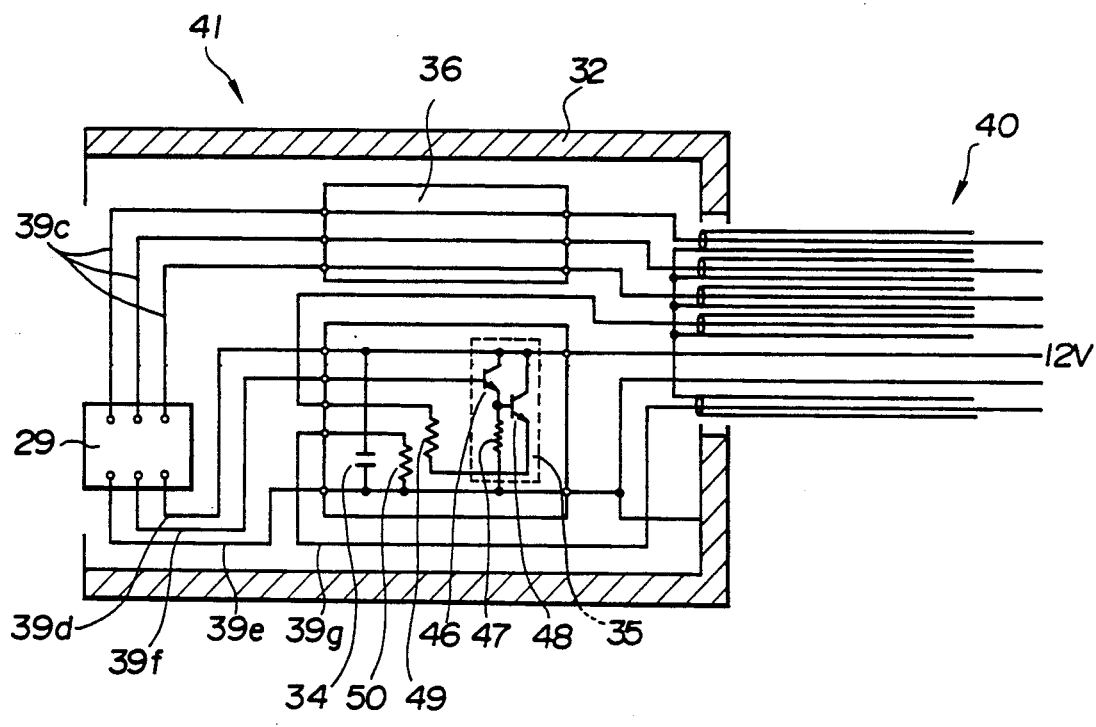

Now, the above mentioned electronic circuit 41 is formed as shown, for example, in FIG. 7.

That is to say, for example, the inside conductors of the three cables 39c set as for driving pulses of the above mentioned signal transmitting cable 40 are connected to the driving pulse inputting terminal of the above mentioned solid state imaging device 29 through the through substrate 36. The cable 39d to which a voltage, for example, of 12 V is set to be applied as for the current source among the above mentioned cables 39 is connected to the current source input terminal of this solid state imaging device 29 and the earthing terminal is connected to the above mentioned shield frame 32 through the cable 39e set as for earthing and is connected to the video processor 3 through the above mentioned signal transmitting cable 40. By the way, to this earthing cable 39e are also connected the outside conductors 39b of the plurality of cables 39.

Further, the output terminal of the above mentioned solid state imaging device 29 is connected to the base of a transistor 46 through a cable 39f set as for the output. The collector of the transistor 46 is connected to the cable 39d for the above mentioned current source. On the other hand, the emitter is connected to the above mentioned cable 39e for earthing and to the base of another transistor. 48. Of this transistor 48, the collector is connected to the above mentioned cable 39d for the current source and the emitter is connected to the above mentioned video processor 3 through a resistance 49.

On the other hand, the above mentioned condenser 34 is arranged between the cable 39d for driving and the cable 39e for earthing and further this cable 39e for earthing is connected to a cable 39g for a dummy through a resistance 50.

In the case of observing a part to be observed with the endoscope 1 formed as in the above, the universal cord 13 is connected to the light source apparatus 2 through the connector 13a and the other universal cord 45 is connected to the video processor 3 through the other connector device 45a. Then the light source apparatus 2 and the current source of the video processor 3 are switched on. The insertable part 8 of the above mentioned endoscope 1 is inserted into a body cavity or a pipe hole. The tip part 12 is directed to the observed part by curving the curvable part 11 with an angle lever not illustrated provided on the operating part 9.

Then, the illuminating light generated by the light source lamp 26 of the above mentioned light source apparatus 2 and condensed by the condenser lens 2c will be led to the tip part 12 by the light guide 14 and will be radiated to the observed part through the light distributing lenses 16 arranged in the illuminating through holes 15a and 15b provided in a pair in the tip part 12.

The image of this observed part will be formed in the device chip 29f of the solid state imaging device 29 by the objective lens system 27. By switching on the current source of the above mentioned video processor 3, the operation of the imaging apparatus will be started and the image formed in the above mentioned device chip 29f will be photoelectrically converted and will be amplified by the signal amplifying IC 35. This amplified signal will be input into the above mentioned video processor 3 through the signal transmitting cable 40, will be processed by the signal processing circuit provided within the video processor 3 and will be output to the monitor 4 so that the image of the above mentioned observed part may be displayed in the picture 4a of the monitor 4.

Now, when the above mentioned signal amplifying IC 35 is operated, heat will be generated in this signal amplifying IC 35 and will be transmitted to the circuit substrate 33 to which the signal amplifying IC is fixed. The circuit substrate 33 is formed of ceramics and is therefore low in the thermal conductivity. The inside conductor 39a of the cable 39 is fixed by soldering to the part opposed to the above mentioned signal amplifying IC 35 of this circuit substrate 33. That is to say, the distance on the circuit substrate 33 between the above mentioned inside conductor 39a at the above mentioned signal amplifying IC 35 side end and the above mentioned signal amplifying IC 35 is shorter than the distance on the circuit substrate 33 between the above mentioned solid state imaging device 29 and the above mentioned signal amplifying IC 35 so that the thermal conductivity to the above mentioned cable 39 side of the heat generated from the above mentioned signal amplifying IC 35 may be higher than the thermal conductivity to the solid state imaging device 29 side of the above mentioned heat. Therefore, substantially all the heat transmitted to the circuit substrate 33 from the signal amplifying IC 35 will be transmitted to the above mentioned inside conductor 39.

By being transmitted to the base end side of the cable 39 through this inside conductor 39a, the above mentioned heat will be prevented from being transmitted to the tip side and base end side of the circuit substrate 33 through the circuit substrate 33.

The above mentioned signal amplifying IC 35 is fixed to the part opposed to the solid state imaging device 29 with the condenser 34 between, that is, to the part separated as much as possible from this solid state imaging device 29 and the cable fixing member 38 formed of a metal is fixed by soldering to the base end side of the above mentioned circuit substrate 33. Therefore, the heat to be transmitted through the above mentioned circuit substrate 35 from the signal amplifying IC 35 will be transmitted to the base end side through the above mentioned cable 39 through this cable fixing member 38 and will be transmitted to the shield frame 32 through the electroconductive bonding agent 52 to be radiated by this shield frame 32. Therefore; it will be very difficult for the heat to be transmitted to the solid state imaging device 29 side having a comparatively long distance and the temperature rise of this solid state imaging device 29 will be avoided.

Also, the heat transmitted to the sealing resin covering this signal amplifying IC 35 from the above mentioned signal amplifying IC 35 will be transmitted to the potting agent 37 for radiating heat set between the above mentioned circuit substrate 33 and through substrate 36 and will be radiated through the potting agent 37.

Thus, the heat generated in the above mentioned signal amplifying IC 35 will be transmitted to the base end side through the cable 39 or will be radiated through the potting agent 37 and therefore will not be transmitted to the solid state imaging device 39, the temperature rise of this solid state imaging device 39 will be prevented, the image deterioration by heat noise will be prevented and the durability of the solid state imaging device 29 will be able to be remarkably elongated. By the way, according to experiments, the temperature of the above mentioned solid state imaging device 39 could be controlled to be 53° C.

In case a therapeutic treatment with the forceps 19 is required in the course of such observation, the forceps 19 is inserted into the inserting port 17b formed in the operating part 9 and is projected to the tip side, that is, toward the above mentioned observed part through the forceps through hole 17 formed in the tip part 12 through a forceps channel not illustrated. Then, this forceps 19 will be displayed at the tip in the picture 4a of the above mentioned monitor 4 and the therapeutic treatment will be possible through this picture 4a.

In such case, the illuminating lights to illuminate the observed part will be radiated from the illuminating through holes 15a and 15b formed in a pair in the above mentioned tip part 12 and the light distributions of the illuminating lights radiated from these illuminating through holes 15a and 16b are made to have predetermined peaks. Therefore, the shadow 19a of the above mentioned forceps 19 will not be produced in the picture and will not obstruct the observation and therapy.

By the way, in this embodiment, the signal amplifying IC 35 is used as an example of a heat generating part. However, it is needless to say that, even if this heat generating part is a regulator or the like, stabilizing, for example, a voltage, the temperature rise of the solid state imaging device 29 will be able to be prevented.

In this embodiment, it is presupposed in the explanation that the above mentioned solid state imaging device 29 is for frame sequential type black and white images. However, this solid state imaging device 29 may be of a simultaneous type provided on the front surface with a color mosaic filter so as to obtain color images.

Figure 8:
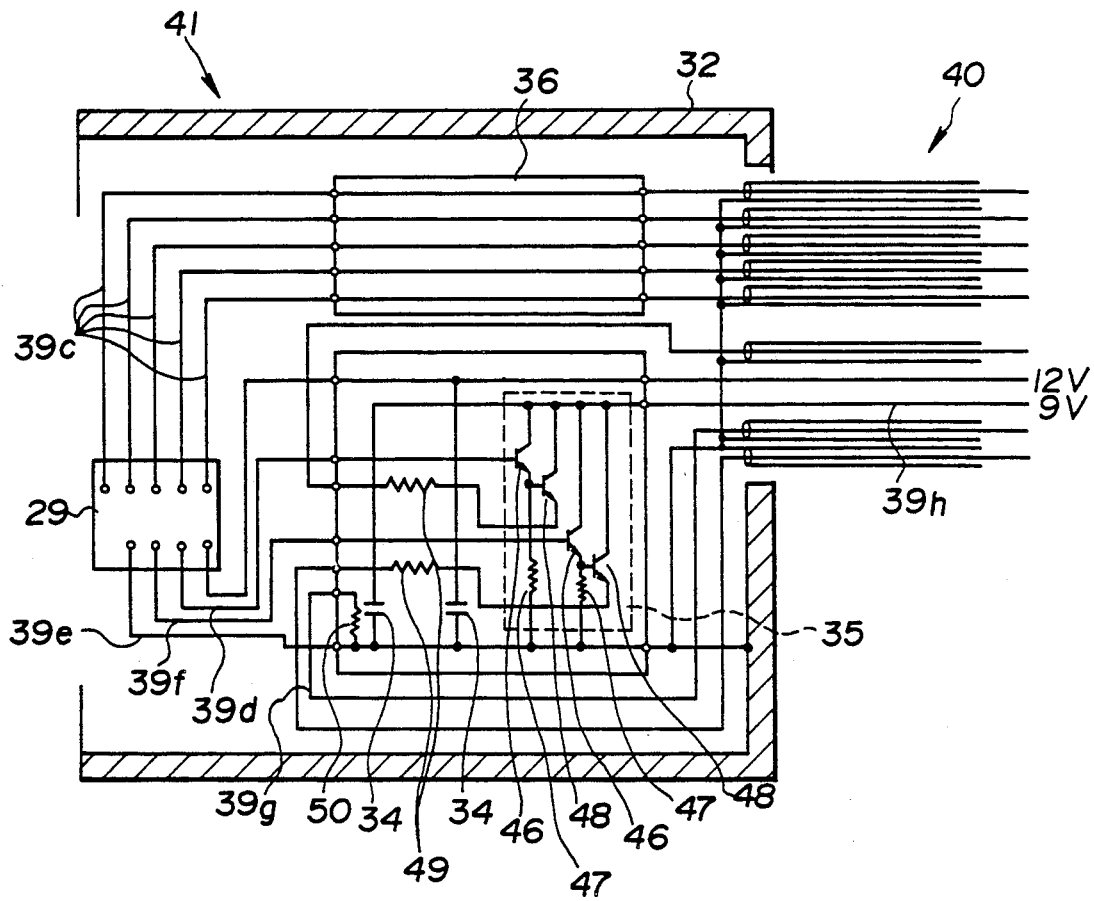
FIG. 8 is a circuit diagram showing an electronic circuit in a modification of the first embodiment.

Now, the above mentioned electronic circuit 41 may be formed as in a modification shown in FIG. 8.

In this modification, the cable 39h is set to transmit a voltage, for example, of 9 V aside from the voltage of 12 V driving the solid state imaging device 29 so as to drive the signal amplifying IC 35 and, on the other hand, the solid state imaging device 29 has a plurality of outputs in response to which the signal amplifying IC 35 is provided with a plurality of the same transistors 46 and 48 as are explained in FIG. 7.

In such formation, the signal amplifying IC 35 driving voltage can be reduced to be lower than in the example shown in FIG. 7, the heat generation by the signal amplifying IC 35 can be inhibited and therefore the temperature rise of the solid state imaging device 29 can be further prevented.

Figure 9:
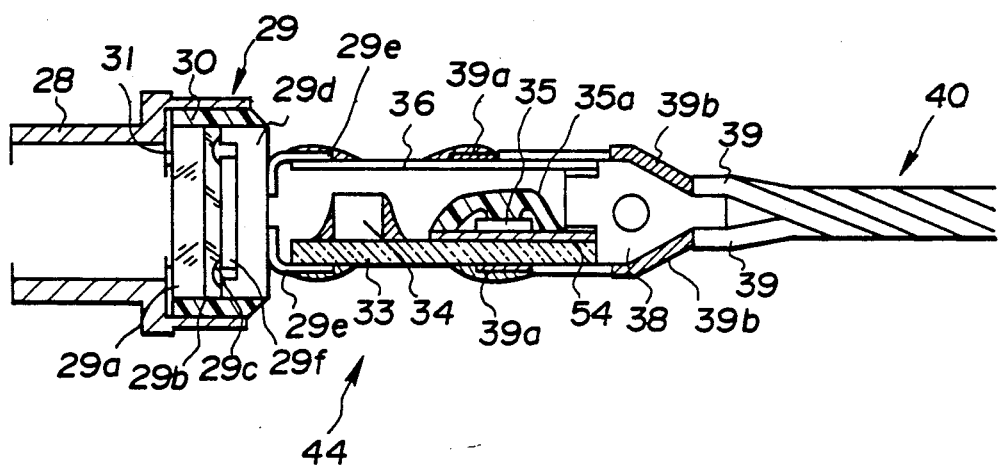
FIG. 9 is a sectioned view of an imaging apparatus of the second embodiment of the present invention.

In FIG. 9 is shown the second embodiment of the present invention. By the way, the same members as are explained in the above described first embodiment and the members of the same operations as therein shall bear the same reference numerals and shall not be explained here.

In this embodiment, the circuit substrate 33 is formed of an adiabatic member and is provided thereon with the electroconductive member 54 formed of a metal plate, continued conductor pattern or gold plating and high in the thermal conductivity and the signal amplifying IC 35 is fixed to this electroconductive member 54 which is in contact on the base end side with the cable fixing member 38. That is to say, the above mentioned electroconductive member 54 leads the heat generated from the signal amplifying IC 35 to the above mentioned cable 39 side at a thermal conductivity higher than the thermal conductivity to the solid state imaging device 29 side.

By such formation, even if the signal amplifying IC 35 generates heat, this heat will be transmitted to the cable fixing member 39 through the electroconductive member 54 and to the cable 39 through this cable fixing member 39. As the circuit substrate 33 is formed of an adiabatic member, it is difficult for heat to be transmitted to this circuit substrate 33. Even if heat is transmitted, it will be transmitted to the inside conductor 39a of the cable 39 fixed to the part opposed to the above mentioned electroconductive member 54 with the circuit substrate 33 between and will be transmitted to the base end side through this inside conductor 39a and thereby the heat will be prevented from being transmitted to the solid state imaging device 29 side.

The other formations, operations and effects are the same as in the first embodiment.

Figure 10:
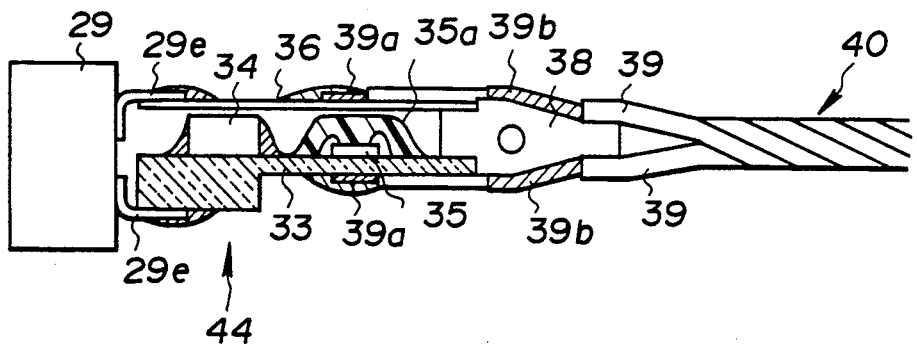
FIG. 10 is a sectioned view of an imaging apparatus of the third embodiment of the present invention.

In FIG. 10 is shown the third embodiment of the present invention.

In this embodiment, the circuit substrate 33 is formed to be thick on the side of the solid state imaging device 29 but to be thin on the side in contact with the cable fixing member 38. As the thermal conductivity will be low on the side formed to be thick but will be high on the side formed to be thin, the heat generated in the signal amplifying circuit 35 and transmitted to the circuit substrate 33 will be transmitted to the cable fixing member 38 substantially through the part formed to be thin of this circuit substrate 35 and will be transmitted to the cable 39. Therefore, the heat transmitted to the side formed to be thick of the circuit substrate 33 will be so little that the temperature rise of the solid state imaging device 29 will be able to be prevented.

The other formations, operations and effects are the same as in the first embodiment.

Figure 11:
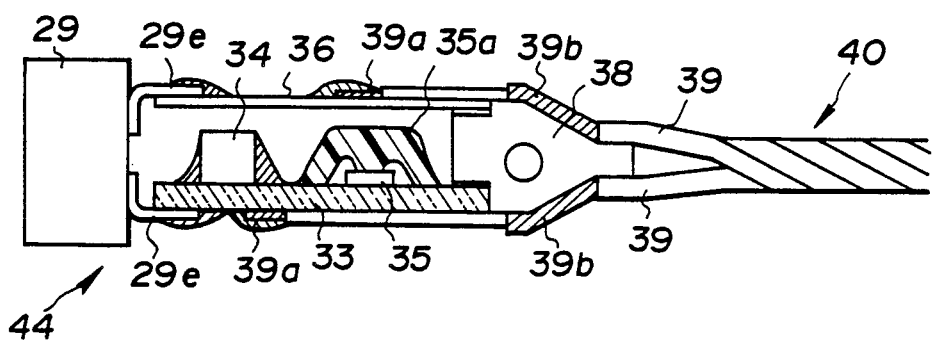
FIG. 11 is a sectioned view of an imaging apparatus of the fourth embodiment of the present invention.

In FIG. 11 is shown the fourth embodiment of the present invention.

In this embodiment, the circuit substrate 33 on the base end side and the cable fixing member 38 made of a metal are fixed in contact with each other, the cable 39 fixed to the above mentioned circuit substrate 33 is extended out beyond the signal amplifying IC 35 and the inside conductor 39a of this cable 39 is fixed to the condenser 34 side. That is to say, the inside conductor 39a is arranged at the end between the signal amplifying IC 35 and the solid state imaging device 29.

In such formation, the heat transmitted to the circuit substrate 33 will be likely to be transmitted to the side of the cable fixing member 38 high in th thermal conductivity. On the other hand, the heat transmitted to the condenser 34 side through the above mentioned circuit substrate 33 will be transmitted to the inside conductor 39a fixed near this condenser 34 and will be thereby prevented from being transmitted to the solid state imaging device 29 side.

The other formations, operations and effects are the same as in the first embodiment.

Figure 12:
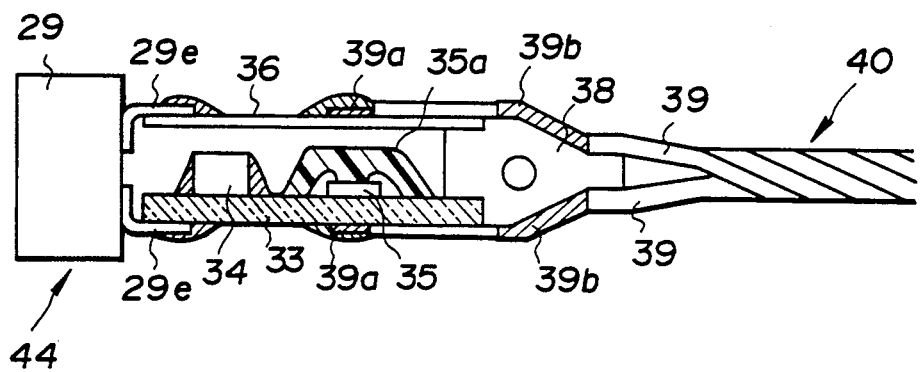
FIGS. 12 and 13 relate to the fifth embodiment of the present invention.
Figure 13:
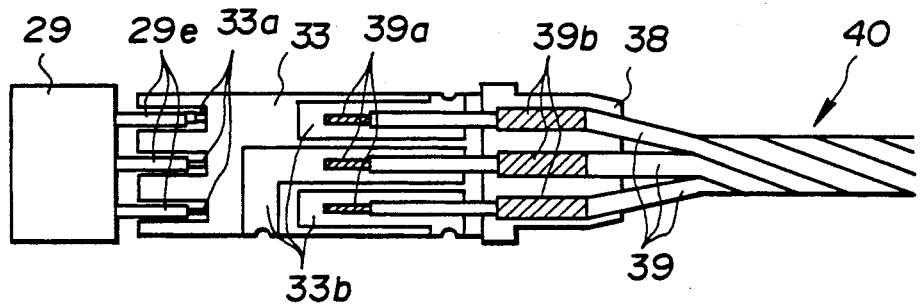

In FIGS. 12 and 13 is shown the fifth embodiment of the present invention.

In this embodiment, as shown in FIG. 13, the area of the land 33b of the circuit substrate 33 in contact with the inside conductor 39a of the cable 39 is formed to be far larger than the area of the land 33a of the circuit substrate 33 in contact with the outside lead 29e.

The heat amount transmitted to the inside conductor 39a through the land 33b having a large area will be larger than the heat amount transmitted to the outside lead 29e through the land 33a having a small area and the heat generated in the signal amplifying IC 35 and transmitted to the circuit substrate 33 will be transmitted to the inside conductor 39a side of the cable 39 through the above mentioned land 33b and will be therefore prevented from being transmitted to the solid state imaging device 29 side through the outside lead 29e.

The other formations, operations and effects are the same as in the first embodiment.

Figure 14:
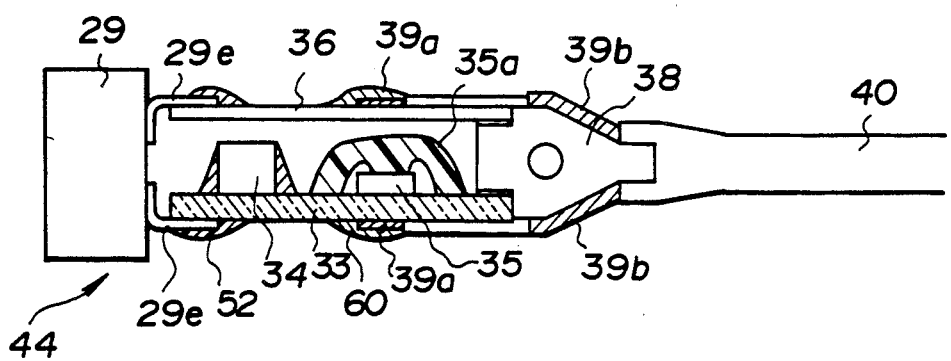
FIG. 14 is a sectioned view of an imaging apparatus of the sixth embodiment of the present invention.

In FIG. 14 is shown the sixth embodiment of the present invention.

In this embodiment, the outside lead 29e of the solid state imaging device 29 and the circuit substrate 33 are fixed to each other with an electroconductive bonding agent 52 and, on the other hand, this circuit substrate 33 and the inside conductor 39a of the cable 39 are fixed to each other by soldering 60.

In case the thermal conductivity of this soldering 60 and the thermal conductivity of the above mentioned electroconductive bonding agent 52 are compared with each other, the thermal conductivity of the soldering 60 will be found to be higher. Therefore, the heat generated in the signal amplifying IC 35 and transmitted to the circuit substrate 33 will be transmitted to the inside conductor 39a side of the cable 39 through this soldering and will be prevented from being transmitted to the solid state imaging device 29 side.

The other formations, operations and effects are the same as in the first embodiment.

Figure 15:
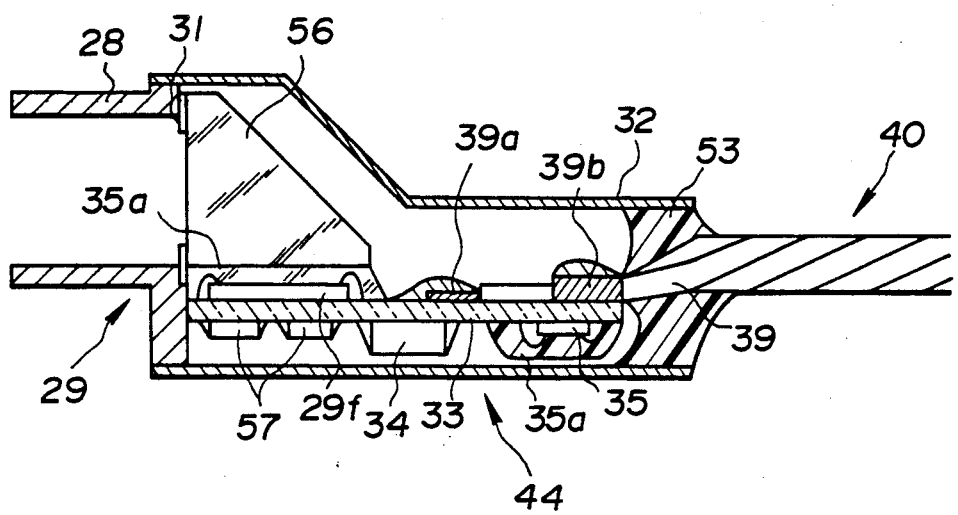
FIG. 15 is a sectioned view of an imaging apparatus of the seventh embodiment of the present invention.

In FIG. 15 is shown the seventh embodiment of the present invention.

In this embodiment, the circuit substrate 33 is formed to be comparatively long and is fitted at the tip side end directly with a device chip 29f so that the optical image may be made to enter the above mentioned device chip 29f by a prism 56. The signal amplifying IC 35 is fixed to the part on the side opposite the part in which the above mentioned device chip 29f is fitted on the lower surface of the above mentioned circuit substrate 35, the condenser 34 is fixed in the substantially middle part on the lower surface of this circuit substrate 35 and such electric device 57 as a resistance is fixed in the part opposed to the above mentioned device chip 29f on the lower surface of the circuit substrate 35.

Further, on the upper surface of the above mentioned circuit substrate 35, the inside conductor 39a of the cable 39 is fixed by soldering in the position substantially intermediate between the signal amplifying IC 35 and the condenser 34 and the outside conductor 39b of this cable 39 is fixed by soldering in the position corresponding to the above mentioned signal amplifying IC 35. The above mentioned cable 39 is fixed on the base end side extended out of the circuit substrate 35 to the shield frame 32 with a reinforcing agent 53.

By such formation, the heat generated in the signal amplifying IC 35 and transmitted to the circuit substrate 33 will be transmitted to the outside conductor 39b of the cable 39 and will be thereby prevented from being transmitted to the device chip 29f side through the circuit substrate 33. Even if the heat is transmitted to the device chip 29f side of the circuit substrate 33, this heat will be transmitted to the inside conductor 39a of the cable 39 fixed to the intermediate part between the above mentioned signal amplifying IC 35 and condenser 34 and therefore the temperature rise of the device chip 29f will be prevented.

Also, as the above mentioned circuit substrate 33 is formed to be comparatively long and the above mentioned signal amplifying IC 35 and device chip 29f are fixed to the tip side end and base end side end and are separated from each other as much as possible, the heat by the above mentioned signal amplifying circuit 33 will be prevented from being transmitted to the device chip 29f side.

The other formations, operations and effects are the same as in the first embodiment.

By the way, in the above first to seventh embodiments, the material of the circuit substrate 33 may be a resin, the material of the inside conductor 39a and outside conductor 39b of the cable 39 may be a gold wire and the material of the cable fixing member 38 may be a copper alloy.

The heat generated from the signal amplifying IC 35 will be transmitted to the solid state imaging device 29 side mostly through the circuit substrate 33. Therefore, if the circuit substrate 33 is made of such material high in the thermal conductivity as a resin and the inside conductor 39a, outside conductor 39b and cable fixing member 38 on the cable 39 side are made of such materials high in the thermal conductivity as the above mentioned metals, the transmission of heat to the solid state imaging device 29 side will be reduced. The above mentioned formation is further effective to the provision of the electroconductive member 54 as shown, particularly, in FIG. 4.

As explained above, according to the first to seventh embodiments, the temperature of the solid state imaging device is prevented from being elevated by the heat of the heat generating part and therefore there are excellent effects that the image photoelectrically converted by this solid state imaging device can be prevented from deteriorating, the durability of this solid state imaging device can be improved and further the apparatus can be prevented from being made large.

In the following eighth to 13th embodiments, the thermal conductivity of the members around the heat generating electronic circuit is made higher than the thermal conductivity of the members around the solid state imaging device so that the heat of the heat generating electronic circuit may be prevented from being transmitted to the solid state imaging device side.

Figure 16:
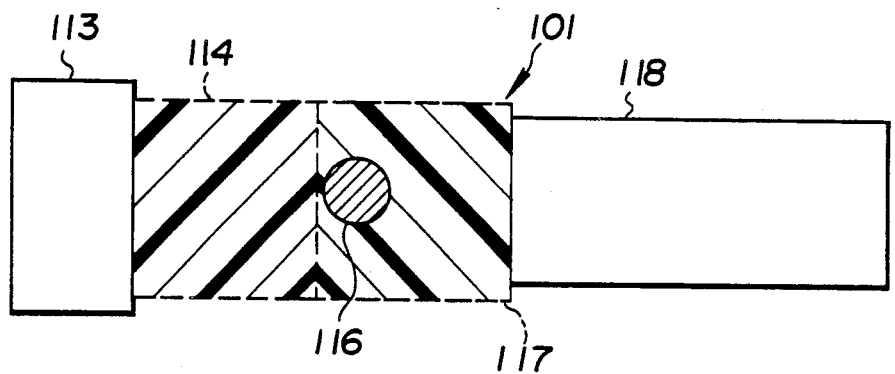
FIGS. 16 to 18 relate to the eighth embodiment of the present invention.
Figure 17:
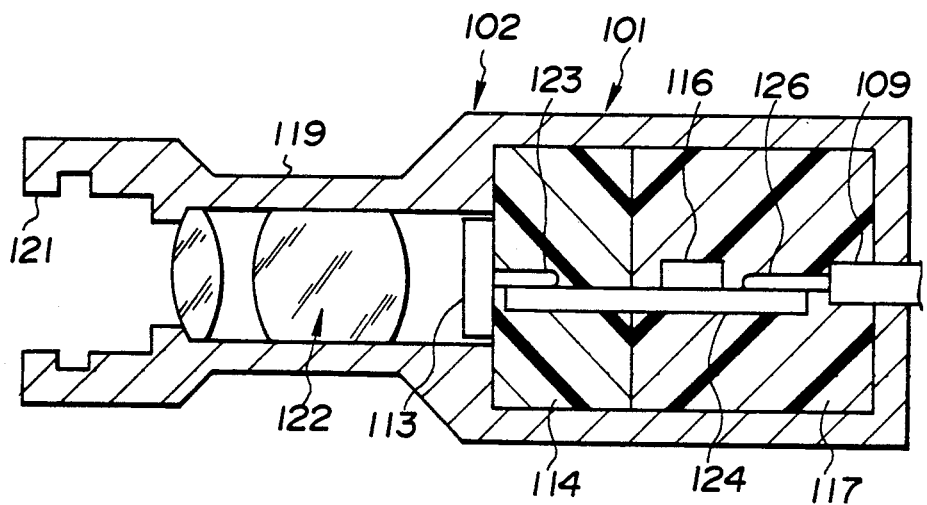
Figure 18:
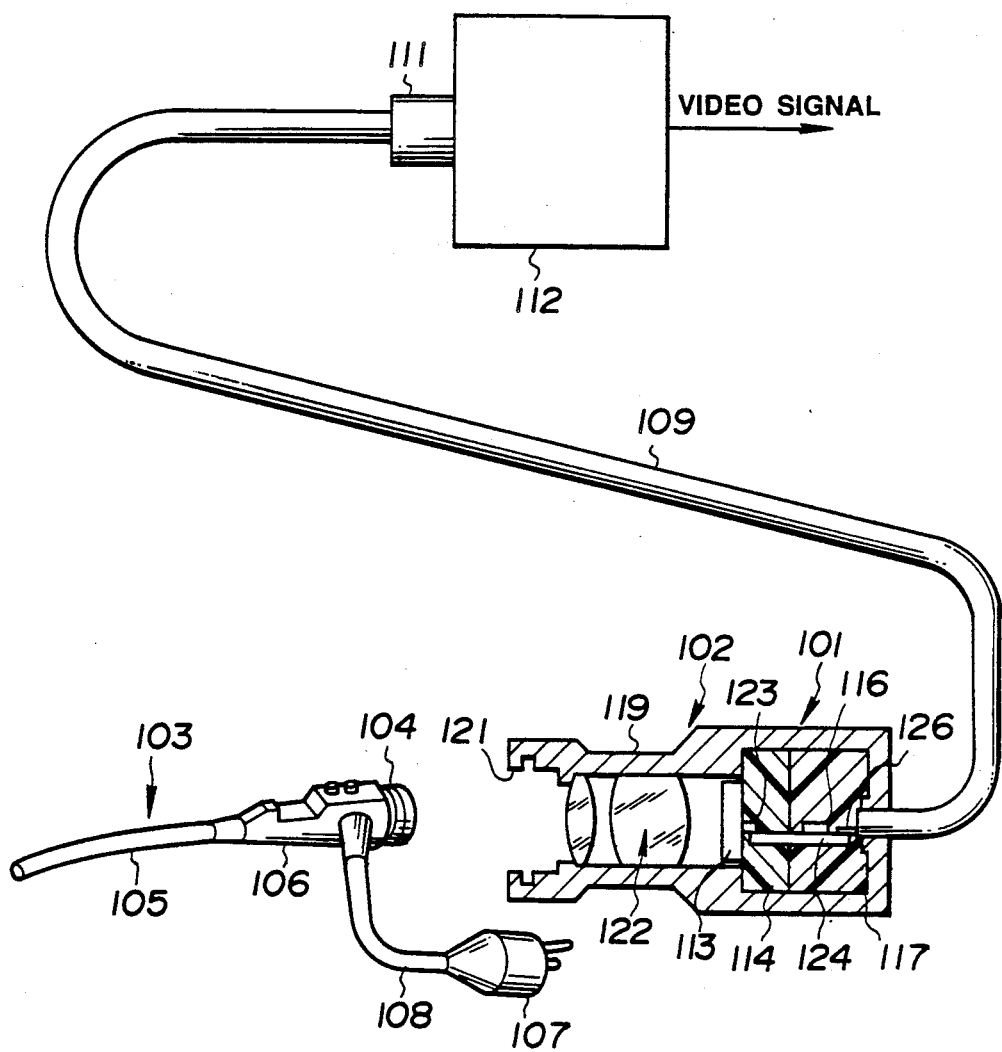

In FIGS. 16 to 18 is shown the eighth embodiment of the present invention.

First of all, the conception of the imaging apparatus of this embodiment shall be explained by using FIG. 16.

On the side opposite the imaging surface in the rear of such solid state imaging device which can image an object to be imaged as, for example, a CCD 113 is provided a first filling member 114 as a first member provided around the CCD 113. In the rear of this first filling member 114 is adjacently provided a second filling member 117 as a second member provided around an electronic circuit 116 electrically connected to the above mentioned CCD 113. In the rear of this second filling member 117 is further provided a processor part or transmitting cable 118 electrically connected with the electronic circuit 116.

Here, if the thermal conductivity of the first filling member 114 is represented by $\alpha$ and the thermal conductivity of the second filling member 117 is represented by $\beta$, $\alpha < \beta$. The heat generated from the electronic circuit 116 within the second filling member 117 will be hard to transmit to the CCD 113 but will be easy to transmit to the processor part or transmitting cable 118 side.

A concrete example of an endoscope system in this embodiment shall be explained by using FIGS. 17 and 18.

In FIG. 18, a camera head 102 having an imaging apparatus 101 built-in is removably provided in an eyepiece part 104 of a fiber scope 103. This fiber scope 103 is provided in the front part with an elongate flexible insertable part 105 and a thick operating part 106 is provided as connected to this insertable part 105 at the rear end. A universal cord 108 which can transmit an illuminating light and is provided at the tip with a light source connector 107 connectable to a light source apparatus not illustrated is extended from the side part of this operating part 106.

A signal cable 109 through which a video signal is to be transmitted is extended from the above mentioned camera head 102 at the rear end and a signal connector 111 provided at the rear end of this signal cable 109 is to be connected to a signal processing apparatus 112 which delivers a video signal to a monitor not illustrated.

The above mentioned camera head 102 is formed of a rigid camera head body 119 within which a connecting part 121 to which the above mentioned eyepiece part 104 can be removably connected is provided in the front part. An objective lens system 122 having the optical axis coincide with that of an eyepiece lens system not illustrated of the above mentioned eyepiece part 104 is positioned and fixed in the rear of this connecting part 121. The imaging plane of the CCD 113 arranged not to be in direct contact with the camera head body 119 is to be positioned in the image forming position of this objective lens system 122. On the side opposite the imaging plane of this CCD 113, a lead part 123 which can input and output a driving signal driving this CCD 113 and a video signal photoelectrically converted by the CCD 113 projects rearward. This lead part 123 is further fitted with such electronic circuit 116 as, for example, a CCD 113 driving circuit or CCD 113 output circuit arranged to be at right angles with the CCD 113 in the rear and is connected to a wired substrate 124. By the way, the material of this substrate may be an alumina-ceramics of a thermal conductivity of 25.2 kcal/m.h. °C. or an epoxy resin of a thermal conductivity of 0.14 kcal/m.h. °C.

A signal line 126 inserted through the above mentioned signal cable 109 is connected to this substrate 124 at the rear end and is connected to the above mentioned signal processing apparatus 112 so as to be able to transmit a video signal and CCD 113 driving signal.

The first filling member 114 low in the thermal conductivity is set in front of the substrate 124 and around the side opposite the imaging plane of the CCD 113 within the above mentioned camera head body 119. The material of this first filling member 114 is air of a thermal conductivity of 0.022 kcal/m.h. °C. or a foaming polystyrene of 0.01 kcal/m.h. °C. Further, the second filling member 117 higher in the thermal conductivity than the first filling member 114 is set in the rear of the substrate 124 and around the electronic circuit 116 fitted on the substrate 124. The material of this second filling member 114 is a heat radiating silicone of a thermal conductivity of 0.9 kcal/m.h. °C., cement of 0.7 kcal/m.h. °C., low melting point glass or ceramics of 25.2 kcal/m.h. °C.

By the way, the substrate 124 may be a flexible substrate formed of a resin or the like.

The operation of the imaging apparatus 101 formed as mentioned above shall be explained.

The camera head 102 connected to the eyepiece part 104 of the fiber scope 103 receives an object image on the imaging plane of the CCD 113. On the other hand, from the signal processing apparatus 112, a driving signal is input into the driving circuit of the electronic circuit 116, has the voltage level adjusted and is applied to the CCD 113. An image signal photoelectrically converted by this driving signal is read out of this CCD 113, is amplified by the output circuit of the electronic circuit 116 and is delivered to the signal processing apparatus 112. The image signal is converted to a video signal by the signal processing apparatus 112. The video signal is output to a monitor not illustrated and the image is displayed on the picture of this monitor.

As the current is amplified in the electronic circuit 116, the generated heat amount is large, is diffused within the second filling member 117 and is transmitted to the camera head body 119, first filling member 114 and signal cable adjacent to the second filling member 117. However, particularly the first filling member 114 is lower in the thermal conductivity than the second filling member 117 and therefore takes time to transmit the generated heat amount. Thus, most of the generated heat amount will be transmitted to the camera head body 119 and signal cable and will be radiated from the signal cable 109. A slight heat amount only from the lead part 123 will be transmitted to the CCD 113 which is not in contact with the camera head body.

As the diffusion of the generated heat amount is made to have a direction as in this embodiment, the heat amount generated by the electronic circuit 116 can be prevented as much as possible from being transmitted to the CCD 113, the increase of the dark current caused by heating the CCD 113 can be prevented and the S/N ratio can be elevated.

Further, as the other effects, the electronic circuit 116 and respective electric contacts can be moisture-proofed and closely sealed and the strength of the entire camera head can be elevated.

Figure 19:
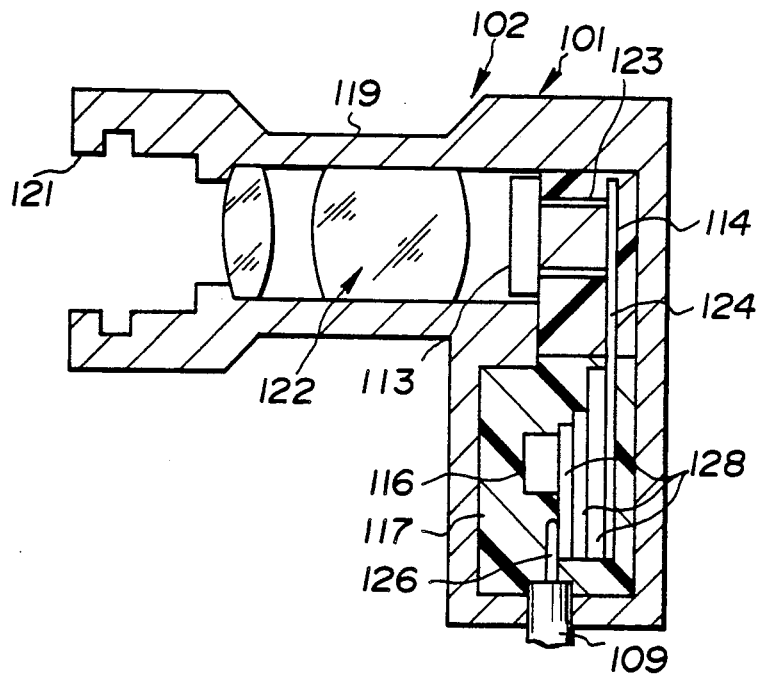
FIG. 19 is an explanatory view showing the formation of a camera head in the ninth embodiment of the present invention.

In FIG. 19 is shown the ninth embodiment of the present invention.

In this embodiment, the substrate 124 is provided so as to face the plane opposite the imaging plane of the CCD 113. By the way, the formations and operations different from those in the eighth embodiment shall be described.

A rigid camera head body 119 forming the camera head 102 having the imaging apparatus 101 built-in is provided in the front part with a connecting part 121 which can be removably connected to the eyepiece part 104. The objective lens system 122 having the optical axis coincide with that of an eyepiece lens system not illustrated of the above mentioned eyepiece part 104 is positioned and fixed in the rear of this connecting part 121. The imaging plane of the CCD 113 arranged so as not to be in direct contact with the camera head body 119 is positioned in the image forming position of this objective lens system 122. The lead part 123 which can deliver an image signal photoelectrically converted by this CCD 113 projects rearward on the side opposite the imaging plane of this CCD 113. This lead part 123 is electrically connected further rearward with the upper part of a substrate 124 arranged to face the plane opposite the imaging plane of the CCD 113. Substrates 128 are laminated on the lower part of this substrate 124. Such electronic circuit 116 as the driving circuit or output circuit of the CCD 113 is fitted on these laminated substrates 128. A signal line 126 inserted through the signal cable 109 is connected to these substrates 128.

The upper part of the substrate 124 and the periphery opposite the imaging plane of the CCD 113 within the camera head body 119 are filled with the first filling member 114 low in the thermal conductivity. The peripheries of the substrates 128 and electronic circuit 116 on the lower part of the substrate 124 are filled with the second filling member 117 high in the thermal conductivity.

The material generally used for the substrate is ceramics high in the thermal conductivity and easy to transmit the generated heat amount. In this case, the transmission of heat can be retarded by laminating the substrates 128 as in this embodiment. Further, the material of the substrate 128 may be partly changed.

The other formations, operations and effects are the same as in the eighth embodiment.

Figure 20:
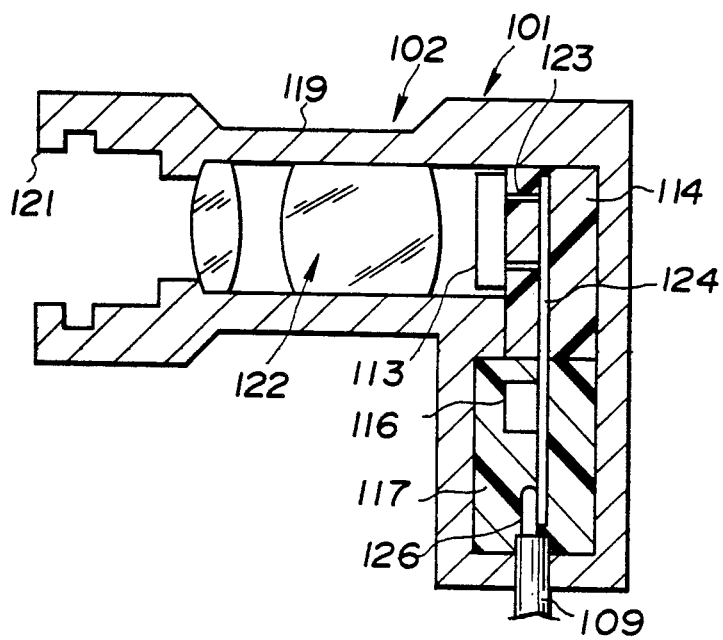
FIG. 20 is an explanatory view showing the formation of a camera head in the tenth embodiment of the present invention.

In FIG. 20 is shown the tenth embodiment of the present invention.

In this embodiment, the substrate 124 faces the plane opposite the imaging plane of the CCD 113.

The imaging plane formed by the CCD 113 is positioned in the image forming position of the objective lens system 122 built-in in the front part of the camera head body 119. The lead part 123 projects rearward in the plane opposite the imaging plane of the CCD 113. The upper part of the substrate 124 arranged to face the plane opposite the imaging plane of the CCD 113 is electrically connected to this lead part 123. The electronic circuit 116 is fitted to the lower part of this substrate 124. The signal line 126 inserted through the signal cable 109 is electrically connected further to the substrate 124 at the lower end.

The peripheries of the plane opposite the imaging plane of the CCD 113 and the substrate 124 within the camera head body 119 are filled with the first filling member 114 low in the thermal conductivity. The periphery of the electronic circuit 116 in the lower part of the substrate 124 is filled with the second filling member 117 high in the thermal conductivity.

The other formations, operations and effects are the same as in the eighth embodiment.

Figure 21:
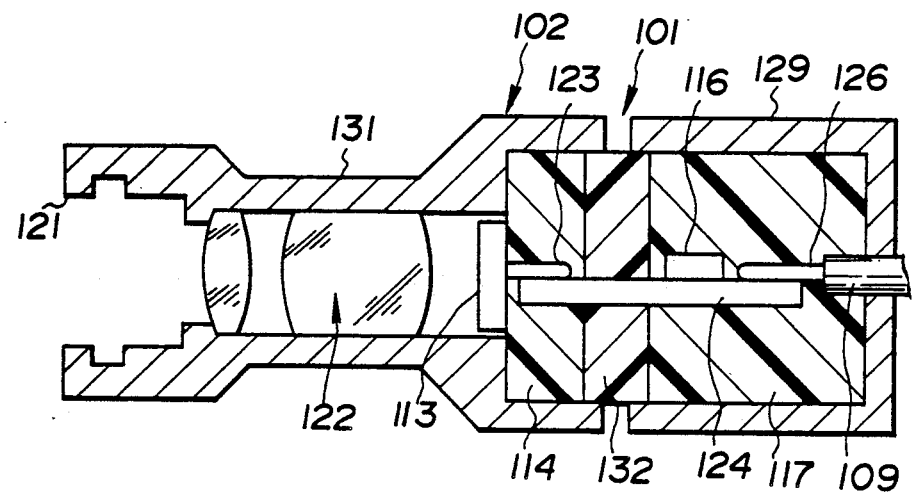
FIG. 21 is an explanatory view showing the formation of a camera head in the 11th embodiment of the present invention.

In FIG. 21 is shown the 11th embodiment of the present invention.

In this embodiment, the camera head 102 supporting the imaging apparatus comprises a camera head tip member 131 as a first supporting member and a camera head base member 129 as a second supporting member. A fixed clearance is kept between these camera head base member 129 and camera head tip member 131 so as not to contact with each other.

The camera head tip member 131 is provided at the tip with a connecting part 121 removably connectable with the eyepiece part 104 of the fiber scope 103. An objective lens system 122 having the optical axis coincide with that of an eyepiece lens system not illustrated provided in the eyepiece part 104 is provided in the rear of this connecting part 121. An imaging plane formed by the CCD 113 is positioned in the image forming position of this objective lens system 122. In the plane opposite the imaging plane of this CCD 113, a lead part 123 is provided to project rearward. The lead part 123 is electrically connected with the front part of a substrate 124 arranged at right angles with the CCD 113. The plane opposite the imaging plane of the CCD 113, the lead part 123 and the front part of the substrate 124 are filled with the first filling member 114 low in the thermal conductivity. The rear part of the substrate 124 projects rearward of the camera head tip member 131. An electronic circuit 116 is fitted in the rear of this projected substrate 124. Further, a signal line 126 inserted through the signal cable 109 is electrically connected to the substrate 124 at the rear end. The rear part of this substrate 124, the electronic circuit 116 and the tip of the signal line 126 are enclosed with the camera head base member 129 and are filled on the periphery with the second filling member 117 high in the thermal conductivity. A third filling member 132 of a thermal conductivity higher than of the first filling member 114 but lower than of the second filling member 117 is set between the first filling member 114 and second filling member 117 to keep the distance between the camera head base member 129 and camera head tip member 131 constant.

By thus providing a fixed distance between the camera head base member 129 and camera head tip member 131, heat will be prevented from being transmitted to the CCD 113 through these members from the electronic circuit 116.

By the way, the thermal conductivity of the third filling member 132 may be lower than of the first filling member 114 and may be lower than of the second filling member 117.

Even in case a camera head is formed of materials high in the thermal conductivity as in this embodiment, heat will be able to be prevented from being transmitted to the camera head tip side having the CCD 113 built-in and the CCD 113 will be able to be prevented from being indirectly heated by the camera head.

The other formations, operations and effects are the same as in the eighth embodiment.

Figure 22:
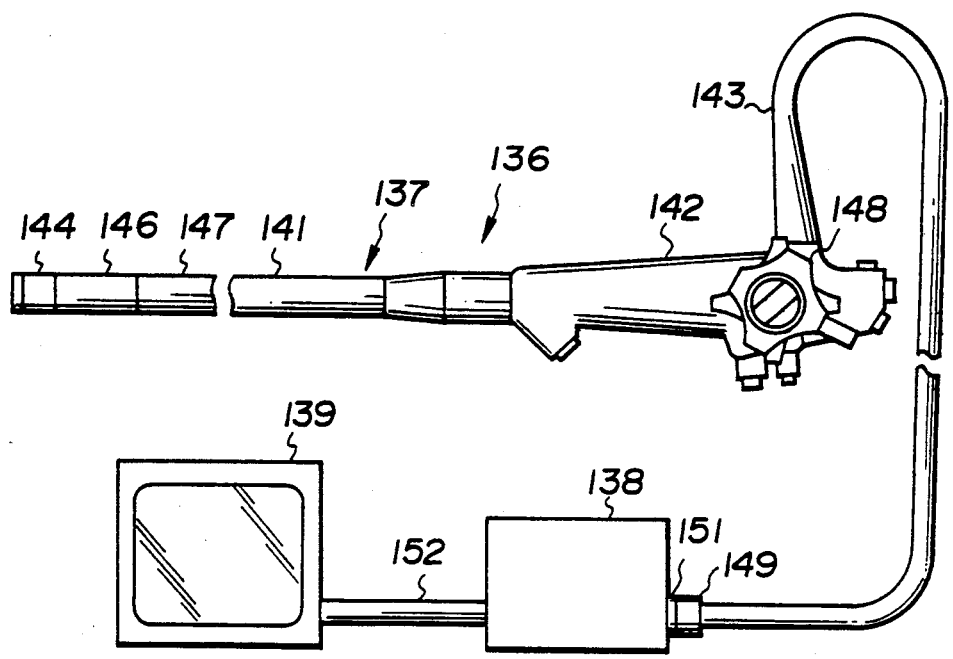
FIGS. 22 and 23 relate to the 12th embodiment of the present invention.
Figure 23:
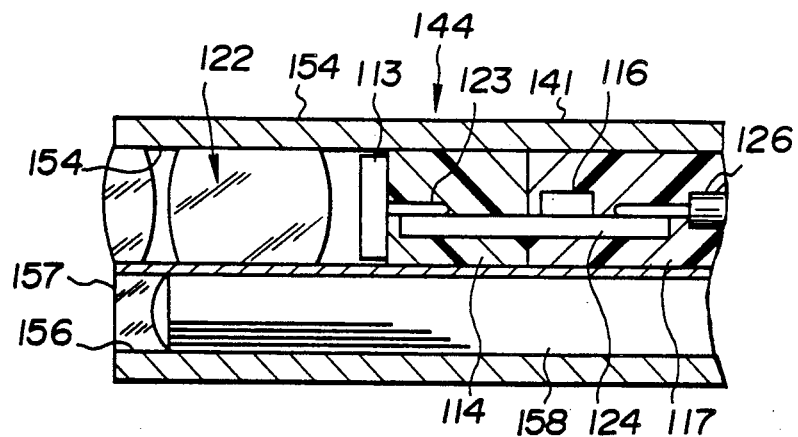

In FIGS. 22 and 23 is shown the 12th embodiment of the present invention.

In this embodiment, the imaging apparatus 101 is built-in in the endoscope tip part.

In FIG. 22, the endoscope system 136 comprises an endoscope 137, a controlling apparatus 138 having a light source part feeding an illuminating light to this endoscope and a signal processing part processing an image signal output from the endoscope 137 and a monitor 139 displaying on a picture a video signal output from this controlling apparatus 138.

The above mentioned endoscope 137 comprises an elongate insertable part 141, a thick operating part provided as connected to this insertable part 141 at the rear end and a light guide and signal cable 143 extended from the side of this operating part.

The above mentioned insertable part 141 is provided on the tip side with a rigid tip part 144 and is provided in the rear adjacent to this tip part with a curvable part 146. Further, a flexible soft part 147 is provided in the rear of this curvable part 146. The above mentioned curvable part 146 can be curved vertically and horizontally by operating an angle lever 148 provided on the above mentioned operating part 142.

A light guide and signal cable connector 149 is provided at the rear end of the above mentioned light guide and signal cable 143 and is connected to a connector receptacle 151 of the above mentioned controlling apparatus 138.

The above mentioned controlling apparatus 138 is connected with the above mentioned monitor 139 by a signal cable 152.

In FIG. 23, the tip part 144 is provided with a rigid tip body 153. On the tip surface of this tip body 153, an observing through hole 154 and illuminating through hole 156 are provided in the lengthwise direction of the insertable part 141. An objective lens system 122 is fitted and fixed in the front part of the above mentioned observing through hole 154. An imaging plane formed by the CCD 113 is positioned in the image forming position of this objective lens system 122. On the side of the plane opposite the imaging plane of this CCD 113, a lead part 123 is provided to project rearward and is electrically connected to the tip part of a substrate 124 arranged at right angles with the CCD 113. An electronic circuit 116 is fitted to the rear part of this substrate 124. Further, the signal line 126 connected to the controlling apparatus 138 through the light guide and signal cable 143 is electrically connected to the substrate 124 at the rear end.

The plane opposite the imaging plane of the CCD 113, the lead part 123 and the front part of the substrate 124 are filled with the first filling member 114 low in the thermal conductivity and the electronic circuit 116, the rear part of the substrate 124 and the tip part of the signal line 126 are filled with the second filling member 117 high in the thermal conductivity.

A light distributing lens 157 is fitted and fixed in the tip part of the above mentioned illuminating through hole 156. The exit end surface of a light guide 158 inserted through the light guide and signal cable 143 and capable of transmitting the illuminating light emitted from the controlling apparatus 138 is provided in the rear of this light distributing lens 157.

Even in case the imaging apparatus 101 is built-in in the tip part 144 of the endoscope 137 as in this embodiment, the same effects as in the eighth embodiment will be able to be obtained.

The other formations, operations and effects are the same as in the eighth embodiment.

Figure 24:
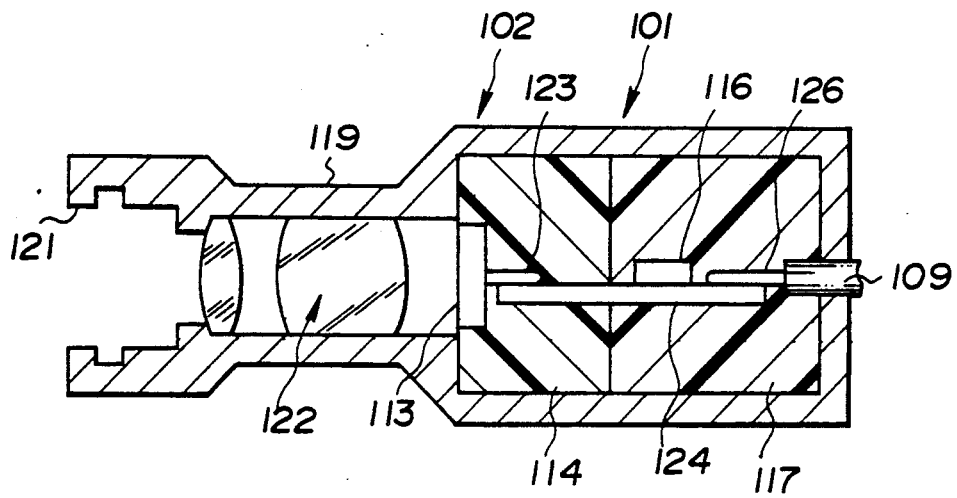
FIG. 24 is an explanatory view showing the formation of a camera head in the 13th embodiment of the present invention.

In FIG. 24 is shown the 13th embodiment of the present invention.

The imaging apparatus 101 of this embodiment is built-in in the camera head 102.

In this embodiment, the plane opposite the imaging plane and four end surfaces of the CCD 113 are filled with a first filling member 114 in the thermal conductivity so as to prevent heat from being transmitted to the CCD 113 from the camera head body 119.

The other formations, operations and effects are the same as in the eighth embodiment.

By the way, in the eighth to 13th embodiments, the substrate 124 is formed of the uniform material to which the invention is not limited. The thermal conductivity may be varied by mixing in impurities or bubbles on the CCD side of the substrate 124.

Further, in the eighth to 11th and 13th embodiments, the present invention is built-in in the camera head but may be built-in in the tip part of the endoscope without being limited to it. Also, in the 12th embodiment, the present invention is built-in in the tip part of the endoscope but may be provided within the camera head without being limited to it.

As described above, according to the eighth to 13th embodiments, as the heat amount diffused from the heat source can be varied by the direction, of the total heat amount diffused from the heat source, the heat amount radiated to the solid state imaging device can be effectively reduced and the airtight effect by sealing is effective to protect the electric part.

It is apparent that, in this invention, working modes different in a wide range can be formed on the basis of this invention without deviating from the spirit and scope of the invention. This invention is not restricted by its specific working mode except being limited by the appended claims.

What is claimed is:

1. An imaging apparatus comprising:
    a solid state imaging device for imaging an object to be imaged;
    an electronic circuit connected operatively to said solid state imaging device and generating heat; and
    a heat conducting means for leading said heat in a direction different from said solid state imaging device side at a thermal conductivity higher than the thermal conductivity of said heat generated from said electronic circuit to said solid state imaging device side.

2. An imaging apparatus according to claim 1 wherein said heat conducting means includes a cable connected operatively to said electronic circuit.

3. An imaging apparatus according to claim 2 further comprising a circuit substrate to which said solid state imaging device, electronic circuit and cable are fixed, the distance on said circuit substrate between said cable a said electronic circuit side end and said electronic circuit being shorter than the distance on said circuit substrate between said solid state imaging device and said electronic circuit so that the thermal conductivity of said heat to said cable side may be higher than the thermal conductivity of said heat to said solid state imaging device side.

4. An imaging apparatus according to claim 2 wherein said heat conducting means further includes a member arranged between said electronic circuit and said cable and leading said heat to said cable side at a thermal conductivity higher than the thermal conductivity of said heat to said solid state imaging device side.

5. An imaging apparatus according to claim 2 wherein said heat conducting means further includes a circuit substrate to which said solid state imaging device, electronic circuit and cable are fixed and the thickness of said circuit substrate between said electronic circuit and said solid state imaging device is larger than the thickness of said circuit substrate between said electronic circuit and said cable so that the thermal conductivity of said heat to said cable side may be higher than the thermal conductivity of said heat to said solid state imaging device side.

6. An imaging apparatus according to claim 2 further comprising a circuit substrate to which said solid state imaging device, electronic circuit and cable are fixed, said cable at said electronic circuit side end being arranged between said solid state imaging device and said electronic circuit on said circuit substrate so that the thermal conductivity of said heat to said cable side may be higher than the thermal conductivity of said heat to said solid state imaging device side.

7. An imaging apparatus according to claim 2 wherein said heat conducting means further includes a circuit substrate to which said solid state imaging device, electronic circuit and cable are fixed, said circuit substrate has a first land to which said solid state imaging device is connected and a second land to which said cable is connected and the area of said second land is larger than the area of said first land so that the thermal conductivity of said heat to said cable side may be higher than the thermal conductivity of said heat to said solid state imaging device.

8. An imaging apparatus according to claim 2 wherein said heat conducting means further includes a circuit substrate to which said solid state imaging device, electronic circuit and cable are fixed, a first fixing means for electrically connecting and mechanically fixing said solid state imaging device to said circuit substrate and a second fixing means for electrically connecting and mechanically fixing said cable to said circuit substrate and the thermal conductivity of said second fixing means is higher than the thermal conductivity of said first fixing means so that the thermal conductivity of said heat to said cable side may be higher than the thermal conductivity of said heat to said solid state imaging device side.

9. An imaging apparatus according to claim 1 wherein said electronic circuit includes an amplifying circuit for amplifying the output signal of said solid state imaging device.

10. An imaging apparatus according to claim 1 wherein said electronic circuit includes a driving circuit giving a driving signal to said solid state imaging device.

11. An imaging apparatus according to claim 1 further comprising a first member arranged between said solid state imaging device and said electronic circuit, said heat conducting means including a second member arranged around said electronic circuit and leading said heat in a direction different from said solid state imaging device side at a thermal conductivity higher than the thermal conductivity of said first member.

12. An imaging apparatus according to claim 11 wherein said first member includes a first filling member set between said solid state imaging device and said electronic circuit, said second includes a second filling member set around said electronic circuit and the thermal conductivity of said second filling member is higher than the thermal conductivity of said first filling member.

13. An imaging apparatus according to claim 11 wherein said heat conducting means further includes a cable connected operatively to said electronic circuit and contacting said second member.

14. An imaging apparatus according to claim 11 further comprising a third member provided between said first member and said second member and having a thermal conductivity lower than the thermal conductivity of said second member.

15. An imaging apparatus according to claim 11 further comprising a first supporting member provided around said first member and a second supporting member provided around said second member, said first supporting member and said second supporting member being separated from each other not to contact with each other.

16. An imaging apparatus according to claim 12 further comprising a supporting member provided around said first filling member and said second filling member, said first filling member being set also between said solid state imaging device and said supporting member so that said solid state imaging device and said supporting member may not contact with each other.

17. An endoscope apparatus comprising:
an elongate insertable part including an observing window in a tip part;
an image forming optical system receiving a light incident through said observing window from an object to be imaged and forming an image of the object;
a solid state imaging device for imaging said object image formed by said image forming optical system;
an electronic circuit connected operatively to said solid state imaging device and generating heat; and
a heat conducting means for leading said heat in a direction different from said solid state imaging device side at a thermal conductivity higher than the thermal conductivity of said heat to said solid state imaging device side.

* * * * *